(12) United States Patent
Gu et al.

(10) Patent No.: US 10,188,370 B2
(45) Date of Patent: Jan. 29, 2019

(54) ULTRASOUND IMAGING SYSTEM AND METHOD

(71) Applicant: KONINKLIJKE PHILIPS N.V., Eindhoven (NL)

(72) Inventors: Xiaolin Gu, Shanghai (CN); Vijay Thakur Shamdasani, Kenmore, WA (US); Yinhui Deng, Shanghai (CN); Xiaomin Li, Shanghai (CN); Ying Wu, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/323,833

(22) PCT Filed: Dec. 18, 2015

(86) PCT No.: PCT/EP2015/080552
§ 371 (c)(1),
(2) Date: Jan. 4, 2017

(87) PCT Pub. No.: WO2016/097320
PCT Pub. Date: Jun. 23, 2016

(65) Prior Publication Data
US 2017/0196539 A1    Jul. 13, 2017

(30) Foreign Application Priority Data

Dec. 18, 2014   (WO) ................ PCT/CN2014/094252
Feb. 19, 2015   (EP) .................................... 15155780

(51) Int. Cl.
*A61B 8/00*    (2006.01)
*A61B 8/08*    (2006.01)

(52) U.S. Cl.
CPC .............. *A61B 8/481* (2013.01); *A61B 8/085* (2013.01); *A61B 8/463* (2013.01); *A61B 8/483* (2013.01); *A61B 8/5223* (2013.01)

(58) Field of Classification Search
CPC ........... A61B 8/481; A61B 8/00; A61B 8/085; A61B 8/483; A61B 8/463; A61B 8/5223
See application file for complete search history.

(56) References Cited

U.S. PATENT DOCUMENTS 5,577,505 A    11/1996   Brock Fisher et al.
5,706,819 A    1/1998    Hwang et al.
(Continued)

FOREIGN PATENT DOCUMENTS

JP    2009225943 A    10/2009
JP    2011115457 A    6/2011
(Continued)

OTHER PUBLICATIONS

Furman-Haran, et al., "Magnetic Resonance Imaging Reveals Functional Diversity of the Vasculature in Bening and Malignant Breast Lesions", 2005 American Cancer Society, Vascular Parameters of Breast Lesions, Aug. 15, 2005, vol. 104, No. 4, pp. 708-718.

*Primary Examiner* — Joel Lamprecht (57) ABSTRACT

The present invention proposes an ultrasound imaging system and a method of calculating a perfusion parameter ratio. The proposed approach comprises: acquiring a time intensity curve of a contrast agent for each region unit of a plurality of region units of an imaging region of a subject, each region unit comprising one or more points of the imaging region; selecting, among the plurality of region units, a first, second and third sets of region units respectively corresponding to normal tissue, vessel and background noise, based on the time-intensity curves; calculating a perfusion parameter for each of one or more region units of the first set of region units and a perfusion parameter for
(Continued)

a region of interest in the imaging region based on the calculated time-intensity curves; calculating a reference perfusion parameter based on the perfusion parameters of the one or more region units; and calculating a ratio value for the region of interest as a ratio of the perfusion parameter of the region of interest and the reference perfusion parameter. Since the reference perfusion parameter is calculated based on the one or more region units which are automatically selected, the approach requires no manual manipulation and the calculated perfusion parameter ratios are independent of operator experience.

14 Claims, 4 Drawing Sheets

(56) References Cited

U.S. PATENT DOCUMENTS

| | | | |
|---|---|---|---|
| 5,833,613 A | 11/1998 | Averkiou et al. | |
| 5,951,478 A | 9/1999 | Hwang et al. | |
| 6,692,438 B2 | 2/2004 | Skyba et al. | |
| 7,248,725 B2* | 7/2007 | Zwirn | G06T 7/0012 382/128 |
| 7,347,821 B2 | 3/2008 | Skyba et al. | |
| 7,756,562 B2 | 7/2010 | Kimura | |
| 2005/0065432 A1 | 3/2005 | Kimura | |
| 2009/0124907 A1* | 5/2009 | Bruce | A61B 8/481 600/458 |
| 2011/0208061 A1 | 8/2011 | Chang | |
| 2012/0082359 A1* | 4/2012 | Arditi | A61B 8/06 382/131 |
| 2013/0084246 A1* | 4/2013 | Moats | G06T 7/0012 424/9.3 |
| 2013/0144165 A1* | 6/2013 | Ebbini | A61B 8/4488 600/439 |

FOREIGN PATENT DOCUMENTS

| | | |
|---|---|---|
| JP | 5478832 B2 | 4/2014 |
| WO | 2005054898 A1 | 6/2005 |
| WO | 2005099579 A1 | 10/2005 |
| WO | 2006090309 A2 | 8/2006 |
| WO | 2009093211 A1 | 7/2009 |

* cited by examiner

ULTRASOUND IMAGING SYSTEM AND METHOD

This application is the U.S. National Phase application under 35 U.S.C. § 371 of International Application No. PCT/EP2015/080552, filed on Dec. 18, 2015, which claims the benefit of Chinese Application No. PCT/CN2014/094252, filed Dec. 18, 2014, and European Application Serial No. 15155780.8, filed Feb. 19, 2015. These applications are hereby incorporated by reference herein.

FIELD OF THE INVENTION

The present invention relates to ultrasound imaging, particularly to contrast-enhanced ultrasound imaging.

BACKGROUND OF THE INVENTION

Contrast-enhanced ultrasound plays an increasingly important role in the characterization of tumors of various organs. In contrast-enhanced ultrasound imaging, the ultrasound data of an imaging region corresponding to a target organ or location of a body is continuously acquired when contrast agent washes into and out of the imaging region. In order to have quantitative measures for the wash-in and wash-out process of the contrast agent, a time-intensity curve that represents the contrast intensity as a function of time is often derived from the ultrasound data and various perfusion parameters may be further derived from the time-intensity curve. Typical perfusion parameters include: area under the curve parameter, peak intensity parameter, time to peak parameter, wash-in time parameter, wash-out time parameter, wash-in rate parameter, wash-out rate parameter, arrival time parameter, mean transit time parameter, rising time parameter, etc.

International patent application WO2009093211A1 (Michalakis et al.) describes that it is desirable that such quantitative measures be repeatable and immune to variations from one imaging procedure to the next, such as variation of the contrast agent injection, patient cardiac output, and ultrasound machine settings which may differ from one examination day to another, and it is proposed to manually identify a region of normal tissue and then compute a wash-in parameter ratio of a region of interest, such as a tumor region, as a ratio of the wash-in parameter of the region of interest and the wash-in parameter of the region of normal tissue. The effects of the aforementioned variations on the wash-in parameter of the region of interest are reduced by dividing it by a reference wash-in parameter, i.e. the wash-in parameter of normal tissue.

However, since different operators may identify different regions as the region of normal tissue, and even the same operator may identify different regions as the region of normal tissue in different imaging procedures, the computed wash-in parameter ratio is dependent on operators' manual manipulations.

US 2005/065432 A1 discloses a blood-flow analysis apparatus for analyzing the time intensity curve for each pixel of region of interest of time-series images collected by photographing a desired region of a sample over time with a mechanical modality by applying a tracer to the blood of the sample. The analysis apparatus includes a calculation unit for calculating parameters indicative of blood-flow dynamics peculiar to the measured tissue of the sample as a ratio to or difference from parameters at a desired reference region on the basis of only the time intensity curve of the measured tissue, and a visual-information presentation unit for visually presenting the calculations by the calculation unit.

SUMMARY OF THE INVENTION

Therefore, it would be advantageous to provide an improved ultrasound imaging system and method of calculating a perfusion parameter of a contrast agent.

In accordance with an embodiment of a first aspect of the present invention, there is proposed an ultrasound imaging system. The ultrasound system comprises: an ultrasound probe configured to acquire a sequence of ultrasound data of an imaging region of a subject when a contrast agent is perfused in the imaging region; a time-intensity curve calculator configured to calculate a time-intensity curve of the contrast agent for each region unit of a plurality of region units of the imaging region, based on the acquired sequence of ultrasound data, each region unit comprising one or more points of the imaging region; a reference selector configured to select, among the plurality of region units, a first, second and third set of region units respectively corresponding to normal tissue, vessel and background noise, based on the time-intensity curves; a perfusion parameter calculator configured to calculate a perfusion parameter for each of one or more region units of the first set of region units and a perfusion parameter for a region of interest in the imaging region, based on the calculated time-intensity curves; a reference perfusion parameter calculator configured to calculate a reference perfusion parameter, based on the perfusion parameters of the one or more region units; and a ratio calculator configured to calculate a ratio value for the region of interest as a ratio of the perfusion parameter of the region of interest and the reference perfusion parameter. The person skilled in the art would appreciate that the first set of region units corresponding to normal tissue refers to a set of region units of which each region unit corresponds to normal tissue, and a region unit corresponding to normal tissue refers to a region unit where its image value indicate that normal tissue is located. Analogy thereto, a region unit corresponding to vessel refers to a region unit where its image value indicate that vessel is located, and a region unit corresponding to background noise refers to region unit where its image value belongs to background noise.

In this way, the reference perfusion parameter is calculated based on the automatically selected first, second and third sets of region units which correspond respectively to normal tissue, vessel and background noise, and therefore, the calculation of the reference perfusion parameter requires no manual manipulation, and thus the calculated reference perfusion parameters are operator-independent. Furthermore, the inventors of the present application have recognized that almost each region unit falls into one of the following three classifications: normal tissue, vessel and background noise, and propose to make use of such prior-knowledge to select all the first, second and third sets of regions respectively corresponding to normal tissue, vessel and background noise, which results in more reliable identification of normal tissue and/or better differentiation of normal tissue from the others like vessel and background noise.

The imaging region can be a 2D imaging plane or a 3D imaging volume. The perfusion parameters can be any kind of parameters currently defined, such as: area under the curve parameter, peak intensity parameter, time to peak parameter, wash-in time parameter, wash-out time parameter, wash-in rate parameter, wash-out rate parameter, arrival time parameter, mean transit time parameter, rising time parameter, or defined in future based on the time-intensity curve.

In case that each region unit comprises more points of the imaging region, the region units can be distinct from each other or can partially overlap.

The one or more region units in the first set of region units can comprise any predetermined number of region units or all region units in the first set of region units. Preferably, the selected one or more region units comprise more than one region units. Typically, in case of a larger number of the selected one or more region units, the calculated reference perfusion parameter can be more stable and/or reliable.

The region of interest can comprise one or more region units. The region of interest can be automatically identified or manually indicated by the operator.

In accordance with a further embodiment of the present invention, the first, second and third sets of region units are selected based on dynamic behavior of the calculated time-intensity curves. The inventors of the present invention recognize that the dynamic behavior of the time-intensity curve indicates how the intensity of the contrast continuously changes over time, and thus can be used to distinguish normal tissue from vessels and background noise. By using the dynamic behavior of the time-intensity curve, the first, second and third sets of region units respectively corresponding to normal tissue, vessel and background noise can be selected in a more reliable way.

In an embodiment, the first, second and third sets of region units are selected based on at least one feature indicating the dynamic behavior of the calculated time-intensity curves. The at least one feature can include any kinds of features indicating the dynamic behavior of the calculated time-intensity curves, such as: area under the curve parameter, peak intensity parameter, time to peak parameter, wash-in time parameter, wash-out time parameter, wash-in rate parameter, wash-out rate parameter, arrival time parameter, mean transit time parameter, rising time parameter.

In another embodiment, the first, second and third sets of region units are selected by inputting the calculated time-intensity curves into a clustering analyzer. Typical clustering analyzer utilizes machine-learning, and is configured to select the first, second and third sets of region units, based on the whole time-intensity curve without any need for predefining any feature. The clustering analyzer can perform any existing clustering methods, such as k means clustering and expectation maximization, or any suitable clustering methods developed in the future. In some embodiments, the clustering analyzer can perform the clustering by starting with a random initial first, second and third sets of region units. In some other embodiments, the clustering analyzer can perform the clustering by starting with predetermined initial first, second, and third sets of regions units.

In accordance with a further embodiment of the present invention, the first, second and third sets of region units are selected by classifying the plurality of region units into the first, second and third sets of region units based on predetermined initial first, second and third sets of region units. The classification can be performed by using a cluster analyzer or any other suitable approach.

In an example, the predetermined initial first, second and third sets of region units can be determined based on one or more statistics about a feature of the time-intensity curve for the plurality of region units. In particular, the feature of the time-intensity curve is one of: area under curve, peak intensity value and mean intensity value, and the one or more statistics comprise mean and standard deviation. In another example, the predetermined initial first, second and third sets of region units can be determined based on historical data and thus can be predetermined prior to acquiring the sequence of ultrasound data of the imaging region.

With the predetermined initial first, second and third set of region units, the classification or clustering based thereon can require less time, and the results can be more reliable.

In accordance with a further embodiment of the present invention, the perfusion parameter calculator is further configured to calculate a perfusion parameter for each region unit of the plurality of region units; and the ratio calculator is further configured to calculate, for each region unit, a ratio value as a ratio of the perfusion parameter of the region unit and the reference perfusion parameter.

In this way, the ratio value is calculated for each region unit of the imaging region. Thus, the ratio values are calculated without the need for setting any region of interest, whether automatically or manually, and the ratio values for all region units can provide more information for the clinician or for further processing steps.

In accordance with a further embodiment of the present invention, the reference selector is further configured to divide the imaging region into a plurality of segments, each segment being located at a different depth level; and to select the one or more region units from the first set of region units, the one or more region units being located in the segment where the region of interest is located. In particular, the reference perfusion parameter calculator can be configured to calculate, for each segment of the plurality of segments, a reference perfusion parameter, based on one or more region units of the selected first set of region units located in that segment.

The inventors of the present invention have recognized that the signal intensity of an ultrasound echo signal decreases as the depth increases, due to acoustic attenuation along the propagation path, and thus the intensity value of the contrast agent for a region unit derived from the ultrasound data is higher than that of a region unit at a deeper location even if there is the same amount of contrast agent. Accordingly, the inventors of the present invention propose not to use always a same reference perfusion parameter for calculating the ratio value regardless of where the region of interest is located, but to use different reference perfusion parameters for regions of interest located at different depth levels. In this way, the various acoustic attenuation levels affecting regions at different depth levels can be reduced or eliminated.

In accordance with a further embodiment of the present invention, the ultrasound imaging system further comprises an image encoder configured to produce corresponding display values for the ratio values; and a display configured to display the display values as a ratio image. Additionally, the image encoder is further configured to encode ratio values with distinctive coloring or shading.

In accordance with an embodiment of a second aspect of the present invention, there is proposed an ultrasound imaging method. The ultrasound imaging method comprises: acquiring a sequence of ultrasound data of an imaging region of a subject when a contrast agent is perfused in the imaging region; calculating a time-intensity curve of the contrast agent for each region unit of a plurality of region units of the imaging region, based on the acquired sequence of ultrasound data, each region unit comprising one or more points of the imaging region; selecting, among the plurality of region units, a first, second and third set of region units respectively corresponding to normal tissue, vessel and background noise, based on the time-intensity curves; calculating a perfusion parameter for each of one or more region units of the first set of regions and a perfusion parameter for a region of interest in the imaging region, based on the calculated time-intensity curves; calculating a reference perfusion parameter based on the perfusion parameters of the one or more region units; and calculating a ratio value for the region of interest as a ratio of the perfusion parameter of the region of interest and the reference perfusion parameter.

In accordance with an embodiment of a third aspect of the present invention, there is provided an apparatus for calculating a perfusion parameter ratio for a region of interest in an imaging region. The apparatus comprises: a receiver configured to receive a time-intensity curve of the contrast agent for each region unit of a plurality of region units of the imaging region, each region unit comprising one or more points of the imaging region; a reference selector configured to select, among the plurality of region units, a first, second and third set of region units respectively corresponding to normal tissue, vessel and background noise, based on the time-intensity curves; a perfusion parameter calculator configured to calculate a perfusion parameter for each of one or more region units of the first set of region units and a perfusion parameter for a region of interest, based on the calculated time-intensity curves; a reference perfusion parameter calculator configured to calculate a reference perfusion parameter, based on the perfusion parameters of the one or more region units; and a ratio calculator configured to calculate a ratio value for the region of interest as a ratio of the perfusion parameter of the region of interest and the reference perfusion parameter.

In accordance with an embodiment of a fourth aspect of the present invention, there is provided a method of calculating a perfusion parameter ratio for a region of interest in an imaging region. The method of calculating a perfusion parameter comprises: receiving a time-intensity curve of a contrast agent for each region unit of a plurality of region units of an imaging region of a subject, each region unit comprising one or more points of the imaging region; selecting, among the plurality of region units, a first, second and third set of region units respectively corresponding to normal tissue, vessel and background noise, based on the time-intensity curves; calculating a perfusion parameter for each of one or more region units of the first set of region units and a perfusion parameter for a region of interest, based on the calculated time-intensity curves; calculating a reference perfusion parameter based on the perfusion parameters of the selected one or more region units; and calculating a ratio value for the region of interest as a ratio of the perfusion parameter of the region of interest and the reference perfusion parameter.

In accordance with an embodiment of a fourth aspect of the present invention, there is provided a computer product, comprising computer program instructions, which, when executed, performs the method of calculating a perfusion parameter.

Other objects and advantages of the present invention will become more apparent and can be easily understood with reference to the description made in combination with the accompanying drawings.

DESCRIPTION OF THE DRAWINGS

The present invention will be described and explained hereinafter in more detail in combination with embodiments and with reference to the drawings, wherein.

The same reference signs in the figures indicate similar or corresponding features and/or functionalities.

DETAILED DESCRIPTION

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

Figure 1:
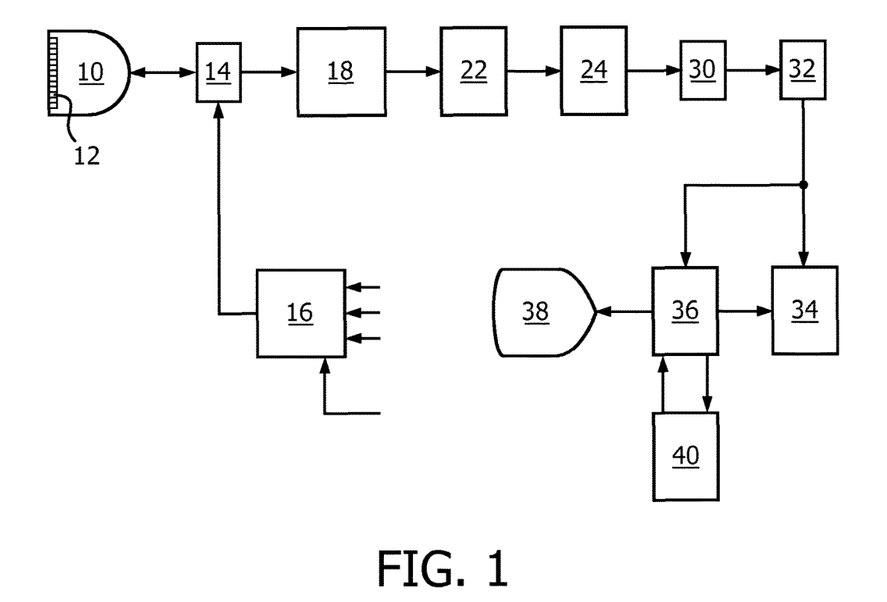
FIG. 1 illustrates, in block diagram form, an ultrasound imaging system constructed in accordance with an embodiment of the present invention.

Referring first to FIG. 1, an ultrasound system constructed in accordance with an embodiment of the present invention is shown in block diagram form. This system operates by scanning a two or three dimensional region of the body being imaged with ultrasonic transmit beams. The two or three dimensional region is often referred to as imaging region. As each beam is transmitted along its steered path through the body, the beam returns echo signals with linear and nonlinear (fundamental and harmonic frequency) components corresponding to the transmitted frequency components. The transmit signals are modulated by the nonlinear response of contrast agent microbubbles encountered by the beam, thereby generating echo signals with harmonic components.

The ultrasound system of FIG. 1 utilizes a transmitter 16 which transmits waves or pulses of a selected modulation characteristic in a desired beam direction for the return of harmonic echo components from scatters within the body. The transmitter is responsive to a number of control parameters which determine the characteristics of the transmit beams, including the frequency components of the transmit beam, their relative intensities or amplitudes, and the phase or polarity of the transmit signals. The transmitter is coupled by a transmit/receive switch 14 to the elements of an array transducer 12 of an ultrasound probe 10. The array transducer can be a one-dimensional array for planar (two-dimensional) imaging or a two-dimensional array for two-dimensional or volumetric (three-dimensional) imaging.

The transducer array 12 receives echoes from the body containing fundamental (linear) and harmonic (nonlinear) frequency components which are within the transducer passband. These echo signals are coupled by the switch 14 to a beamformer 18, which appropriately delays echo signals from the different transducer elements and which then combines them to form a sequence of linear and harmonic signals along the beam from shallow to greater depths. Preferably, the beamformer is a digital beamformer operating on digitized echo signals to produce a sequence of discrete coherent digital echo signals from a near-field to a far-field depth of the image. The beamformer may be a multiline beamformer which produces two or more sequences of echo signals along multiple spatially distinct receive scanlines in response to a single transmit beam, which is particularly useful for 3D imaging. The beamformed echo signals are coupled to an ensemble memory 22.

In the ultrasound system of FIG. 1, multiple waves or pulses are transmitted in each beam direction using different modulation techniques, resulting in the reception of multiple echoes for each scanned point in the image field. The echoes corresponding to a common spatial location are referred to herein as an ensemble of echoes, and are stored in the ensemble memory 22, from which they can be retrieved and processed together. The echoes of an ensemble are combined in various ways by the nonlinear signal separator 24 to produce the desired nonlinear or harmonic signals. For example, two pulses of different phase or polarity modulation can be transmitted to each point in the image field. When the echoes resulting from the two pulses are received by the ultrasound system and additively combined, the different modulation causes the fundamental frequency components of the echoes to cancel each other and the harmonic components to reinforce each other. This separates out the harmonic components of the echo signals. Alternatively, when the two echoes are subtracted from each other, the fundamental frequency components are reinforced and the harmonic components cancel each other. This separates out fundamental frequencies for construction of a standard B mode image. This modulation is referred to as "pulse inversion," and can be done by phase, polarity or amplitude modulation as described in U.S. Pat. No. 5,706,819 (Hwang et al.), U.S. Pat. No. 5,951,478 (Hwang et al.), and U.S. Pat. No. 5,577,505 (Brock Fisher et al.).

The separated signals are filtered by a filter 30 to further remove unwanted frequency components, and then subjected to B mode or Doppler detection by a detector 32. The detected signals are coupled to a nonlinear signal combiner 34 to reduce image speckle content. The signals are then processed for the formation of a two-dimensional, three-dimensional, spectral, parametric, or other desired image in image processor 36, and the image is then displayed on a display 38. Detected fundamental (linear) signals which do not need speckle reduction processing are coupled directly to the image processor 36 for image formation and display.

In accordance with an embodiment of the present invention, the ultrasound image data is also coupled to a QLab image processor 40 for the production of time-intensity curves and contrast agent wash-in and wash-out characteristics. The time-intensity curves and characteristics produced by the QLab processor are coupled back to the image processor where they may be displayed numerically or graphically on the display 38 along with the ultrasound images. A standard QLab processor which is suitable for the production of time-intensity curves is available from Philips Healthcare of Andover, Mass.

A standard QLab processor produces the well-known time-intensity curves, also referred to as perfusion curves or reperfusion curves. See U.S. Pat. No. 5,833,613 (Averkiou et al.), international patent publication WO 2005/099579 (Rafter), international patent publication WO 2005/054898 (Garg et al.), and international patent publication WO2009093211A1 (Michalakis et al.). As these publications illustrate, the build-up of contrast agent at points in the tissue is monitored during the arrival of the contrast agent at locations in the body. The amount of contrast agent at a point is indicated by the intensity of echoes returned from contrast agent microbubbles at each point, and is present in a sequence of images acquired by low power (low MI) transmission as the contrast agent washes into the tissue. A time-intensity curve can be formed of this build-up of contrast intensity and its subsequent decline during wash-out of the contrast agent for each point in the tissue which returns the time sequence of echoes frame-by-frame. A qualitative presentation of the time-intensity curves for the entire tissue being viewed can be formed by coloring each pixel in an anatomical image with a color that represents a parameter of the time-intensity curves at each point in the image. The Garg et al. application illustrates the formation of a parametric image of the myocardium, where the color of each pixel in the image represents the peak level attained by the time-intensity curve at each point in the myocardium, for example. See also U.S. Pat. No. 6,692,438 (Skyba et al.).

In accordance with an embodiment of the present invention, the ultrasound probe is configured to acquire a sequence of ultrasound data of an imaging region of a subject when a contrast agent is perfused in an imaging region, and the QLab imaging processor acting as a time-intensity curve calculator is configured to calculate a time-intensity curve of the contrast agent for each region unit of a plurality of region units of the imaging region, based on the acquired sequence of ultrasound data. Each region unit can comprise one or more points of the imaging region. In some embodiments, a point of the imaging region is defined as a region unit. In some other embodiments, several adjacent points of the imaging region are defined as a region unit. For example, a region unit can have a square dimension of 5×5 in an imaging plane or a cubic dimension of 5×5×5 in an imaging volume. The plurality of region units can be separate or partially overlapping.

Figure 2:
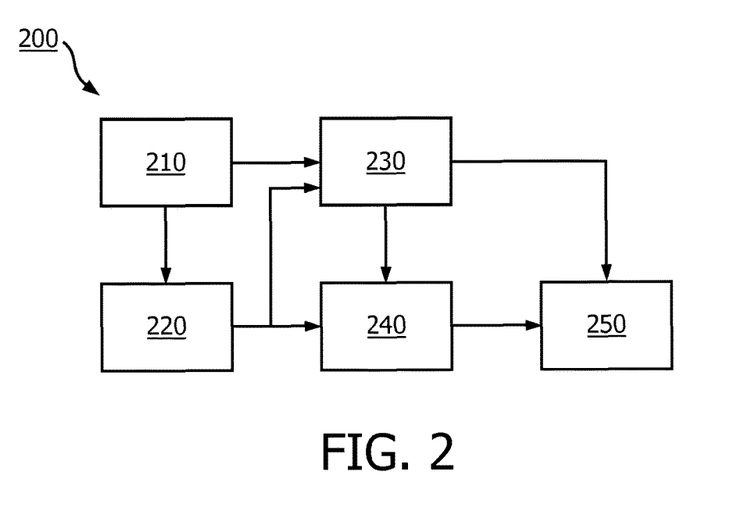
FIG. 2 illustrates, in block diagram form, an apparatus for calculating a ratio value of a perfusion parameter in a contrast-enhanced ultrasound imaging procedure in accordance with an embodiment of the present invention.
Figure 3:
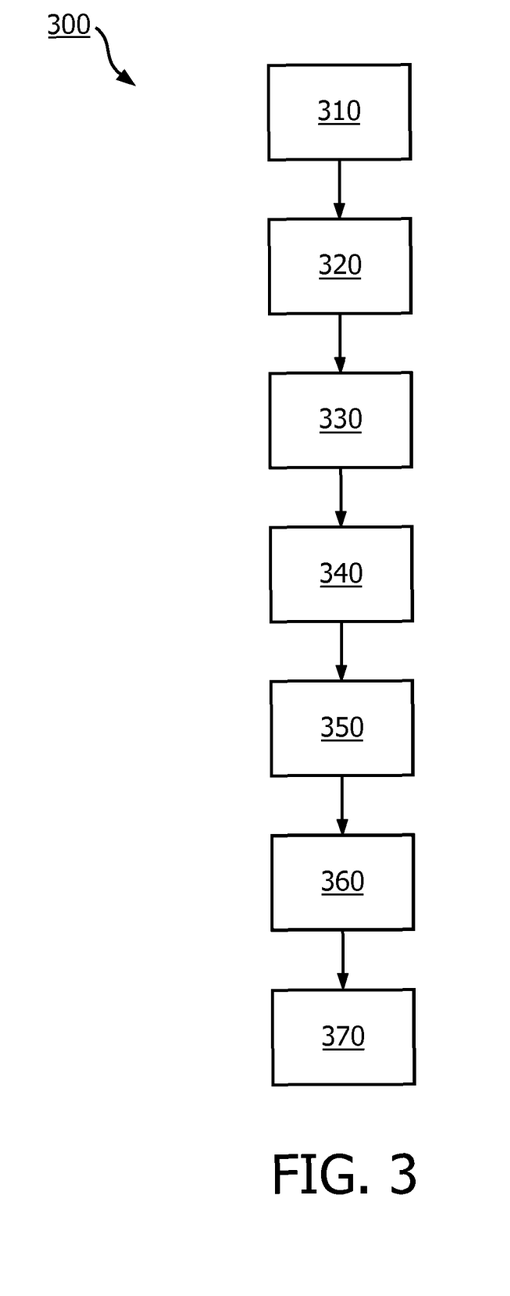
FIG. 3 illustrates, in a block diagram, a method of calculating a ratio value of a perfusion parameter in a contrast-enhanced ultrasound imaging procedure in accordance with an embodiment of the present invention.

As a quantitative measure of the perfusion of the contrast agent, a ratio value of a perfusion parameter is computed for a region of interest in the imaging region. FIG. 2 and FIG. 3 illustrate an apparatus 200 and a method 300 for computing the ratio value of the perfusion parameter in accordance with an embodiment of the present invention, respectively. In some embodiments, the QLab imaging processor 40 is configured to perform the method 300, and thus the apparatus of FIG. 3 is part of QLab image processor 40. In some other embodiments, the apparatus 200 can be a separate processor that can be coupled to the QLab image processor 40. The apparatus 200 can be part of the ultrasound system or can also be a separate processor or part of a separate system that is coupled to the ultrasound system via any kinds of wired or wireless connection means.

Referring to FIG. 2, the apparatus 200 comprises a receiver 210, a reference selector 220, a perfusion parameter calculator 230, a reference perfusion parameter calculator 240 and a ratio calculator 250. The receiver 210 is an interface for receiving a time-intensity curve of the contrast agent for each region unit of a plurality of region units of the imaging region, based on the acquired sequence of ultrasound data, each region unit comprising one or more points of the imaging region. The receiver 210 can be implemented in either software, hardware or a combination thereof.

The calculation of the ratio value will be described hereinafter by referring to FIG. 2 and FIG. 3. While, for the sake of simplicity of explanation, the method is shown and described as a series of steps, it is to be understood and appreciated that the methodology is not limited by the order of steps, as some steps may occur, in accordance with one or more aspects, in different orders and/or concurrently with other steps as compared to the orders and steps shown and described herein. Moreover, not all illustrated steps may be utilized to implement a method in accordance with the claimed subject matter. In general, a process can be implemented as processor instructions, logical programming functions, or other electronic sequence that supports the calculation of the ratio value.

In step 310, a temporal sequence of ultrasound data of an imaging region of a subject, as a contrast agent is perfused in the imaging region, is acquired by placing an ultrasound probe on the subject. Alternatively, the sequence of ultrasound data can be acquired from any data storage where the sequence of the ultrasound data previously acquired by the ultrasound probe is stored, for example, in a DICOM format.

In step 320, a time-intensity curve calculator calculates a time-intensity curve of the contrast agent for each region unit of a plurality of region units of the imaging region, based on the acquired sequence of ultrasound data. Alternatively, the receiver 210 receives, from any data storage, time-intensity curves which are pre-calculated and stored. As is well known to the person skilled in the art, various kinds of motion compensations may be performed prior to the calculation of the time-intensity curves, and/or the time-intensity curves may be smoothed, for example, by means of a low-pass filter.

In step 330, the reference selector 220 selects, among the plurality of region units, a first set of region units corresponding to normal tissue, based on the time-intensity curves, preferably based on the dynamic behavior of the time-intensity curves. In particular, the reference selector 220 can be configured to select a first set of region units corresponding to normal tissue, a second set of region units corresponding to vessel, and a third set of region units corresponding to background noise. In some embodiments, at least one feature indicating the dynamic behavior of the time-intensity curves is calculated and then the first, second and third sets of regions are selected based on the at least one feature. In some other embodiments, each point of the time-intensity curves are regarded as an individual feature, and the selection of the first, second and third sets of regions is directly based on the time-intensity curves.

The selection of the first set of region units can be implemented by means of cluster analysis. Cluster analysis or clustering is well-known: it is the task of grouping a set of objects in such a way that objects in the same group or set (called a cluster) are more similar (in some sense or another) to each other than to those in other groups or sets (clusters).

Figure 4:
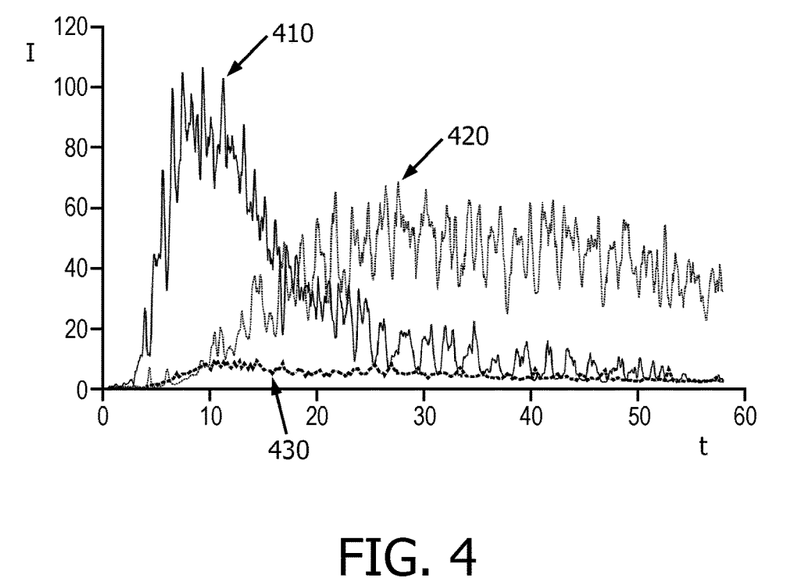
FIG. 4 illustrates a typical time-intensity curve for each of: normal tissue, vessels, and background noise.

FIG. 4 illustrates a time-intensity curve 410 for a vessel, a time-intensity curve 420 for normal tissue, and a time-intensity curve 430 for background noise. Typically, the dynamic behavior of the time-intensity curve, namely the change of the intensity value I over time t, is quite different among vessels, normal tissue and background noise.

In accordance with some embodiments of the present invention, the reference selector 220 classifies the plurality of region units into the first set of region units corresponding to normal tissue, a second set of region units corresponding to vessels, and a third set of region units corresponding to background noise, based on dynamic behavior of the time-intensity curves.

In an embodiment, the classification can be performed based on an initial first, second and third sets of region units. That is, the initial first, second and third sets of region units are used for initialization of the classification.

In some embodiments, such classification can be performed by means of cluster analysis, and thus the initial first, second and third sets of region units are used for initialization of the cluster analysis. Any suitable clustering method can be used, including the existing ones such as k means clustering or expectation maximization, or those developed in the future. The cluster analysis can either be performed based on one or more pre-defined features indicating the dynamic behavior of the time-intensity curves, or it can be performed based directly on the time-intensity curves without defining any features in advance.

The initial first, second and third sets of region units can be determined based on historical data and thus can be predetermined prior to acquiring the sequence of ultrasound data of the imaging region.

Alternatively, a feature is extracted from the time-intensity for each of the plurality of region units, and the initial first, second and third sets of region units are determined based on one or more statistics about the extracted features. In this particular embodiment, the extracted feature is: area under curve. In other embodiments, the extracted feature can be: peak intensity value, mean intensity value of the curve or any other suitable feature. Next, the mean $\mu$ and the standard deviation $\sigma$ of the extracted features are calculated. Then, the initial first, second and third sets of regions can be determined, based on $\mu$ and $\sigma$, as follows:

the initial first set of region units corresponding to normal tissue comprises region units whose feature has a value in the range of $[\mu-\alpha\cdot\sigma, \mu+\alpha\cdot\sigma]$;

the initial second set of region units corresponding to vessels comprises region units whose feature has a value greater than $\mu+\alpha\cdot\sigma$, namely in the range of $[\mu+\alpha\cdot\sigma, +\infty]$; and the initial third set of region units corresponding to background noise comprises region units whose feature has a value less than $\mu-\alpha\cdot\sigma$, namely in the range of $[-\infty, \mu-\alpha\cdot\sigma]$.

$\alpha$ is a pre-determined weighting coefficient. For example, $\alpha$ can be determined by means of experiments.

In step 340, the reference selector 220 further selects one or more region units from the first set of region units. In some embodiments, this step 340 is omitted, and the one or more region units simply comprises all region units in the first set of region units. In some other embodiments, part of the region units of the first set of region units are selected. The number of selected region units can be pre-defined or can be defined by operators.

In step 350, the perfusion parameter calculator 230 calculates a perfusion parameter for each of the selected one or more region units, based on the time-intensity curves. Furthermore, the perfusion parameter calculator 230 calculates a perfusion parameter for a region of interest, based on the time-intensity curves. The perfusion parameter can be any kind of parameter derived from the time-intensity curves, such as: area under the curve parameter, peak intensity parameter, time to peak parameter, wash-in time parameter, wash-out time parameter, wash-in rate parameter, wash-out rate parameter, arrival time parameter, mean transit time parameter, rising time parameter, or it can be defined in the future based on the time-intensity curve.

The region of interest can comprise one or more region units. The region of interest can be a pre-defined region, or a region indicated by a user or identified in any pre-processing step. In case that there are a plurality of regions of interest, a perfusion parameter is calculated for each of the plurality of regions of interest. In some embodiments, each region unit of the plurality of region units is defined as a region of interest. In this way, a perfusion parameter is calculated for each region unit.

The calculation of the perfusion parameters for the region of interest can be performed independently of the selecting steps 330 and 340. The one or more region units and the region of interest may comprise common region units, in which case the person skilled in the art would appreciate that the perfusion parameters of those common region units need only to be calculated once.

In step 360, a reference perfusion parameter calculator 240 calculates a reference perfusion parameter, based on the perfusion parameters of the selected one or more region units. The reference perfusion parameter can be calculated in various ways. For example, the reference perfusion parameter can be calculated as the average, weighted average or median of the perfusion parameters of the selected one or more region units.

In step 370, a ratio calculator 250 calculates a ratio value for the region of interest as a ratio of the perfusion parameter of the region of interest and the reference perfusion parameter. In case that there are a plurality of regions of interest, a ratio value is calculated for each of the plurality of regions of interest. In some embodiments, each region unit of the plurality of region units is defined as a region of interest. In this way, a ratio value r is calculated for each region unit.

The ratio values can then be converted to corresponding display values by means of an image encoder, and the display values can be presented by a display as a parametric ratio image. Depending on the dimension of the image region, the ratio image can be 2D or 3D. The image encoder can be further configured to encode ratio values with distinctive coloring or shading. For example, ratio values in a certain value range can be distinctly colored, such as a bright red color. The clinician is thus enabled to easily spot suspect regions in the ratio image by virtue of the distinctive coloring of even small suspect regions of the image. In some embodiments, the ratio image is smoothed prior to the encoding and displaying.

Figure 5:
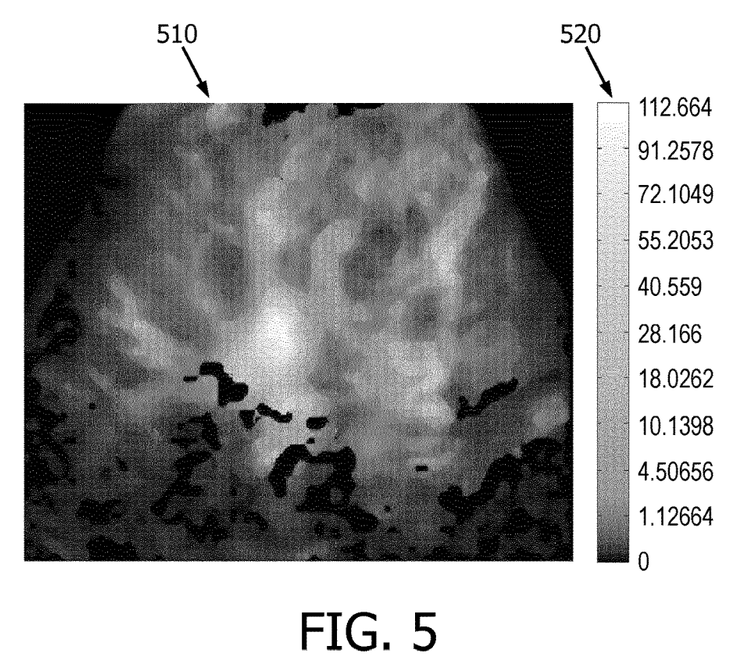
FIG. 5 illustrates an exemplary ratio image.

FIG. 5 illustrates an exemplary ratio image 510 and a color bar 520 at the right side. The ratio image 510 represents the ratio value of the peak intensity of the time-intensity curve. The ratio value is encoded with shading. The color bar 520 shows the coding of the ratio values, particularly higher ratio values being brighter.

As described in the above, a same reference perfusion parameter is used to derive a ratio value for the region of interest, regardless of the depth at which the region of interest is located. Alternatively, a different reference perfusion parameter may be used for a region of interest located at a different depth level. In accordance with another embodiment of the present invention, the reference selector 220 is further configured to divide the imaging region into a plurality of segments, each segment being located at a different depth level, and the one or more region units corresponding to normal tissue used to calculate the reference tissue is located at the same segment where the region of interest is located.

Figure 6:
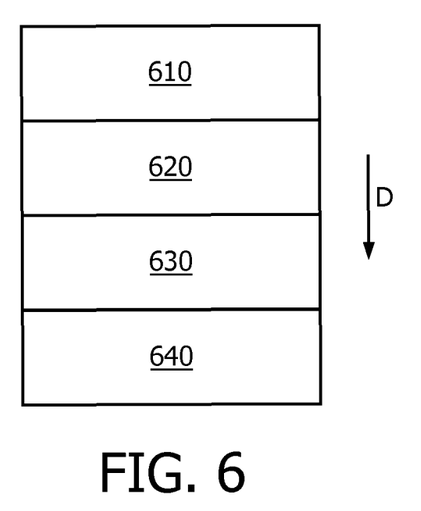
FIG. 6 illustrates an imaging region being segmented into a plurality of segments in accordance with an embodiment of the present invention.

FIG. 6 illustrates a 2D imaging region being segmented into a plurality of segments in accordance with an embodiment of the present invention. Referring to FIG. 6, along the depth direction indicated by arrow D, a plurality of segments 610 to 640 are located at a different depth level, with segment 640 being the deepest. The plurality of segments 610 to 640 are shown to be not overlapping, but in some other embodiments, they can be partially overlapping. Although four segments are illustrated, the person skilled in the art would appreciate that any number of segments is possible. In some embodiments, the number of segments can be dependent on the depth range of the imaging region. For example, the imaging region is divided into more segments if the imaging region spans a wider range in the depth direction.

In accordance with an embodiment of the present invention, a reference perfusion parameter is calculated for each of the plurality of segments of the image region, and then the ratio value for a region unit is calculated based on the reference perfusion parameter for the segment where that region unit is located. For example, the ratio value for a region unit can be calculated as a ratio of the perfusion parameter for that region unit and the reference perfusion parameter for the segment where that region unit is located. For a region unit located at the border of a segment or at more than one segment in case of the segments being partially overlapping, the reference perfusion parameter used for that region unit can be a weighted average of the reference perfusion parameters of the corresponding segments.

The reference perfusion parameter for each segment can be calculated in different ways.

In some embodiments, the cluster analysis is performed over the whole imaging region to get the first set of region units that corresponds to normal tissues in the whole imaging region. Then, for each segment, a reference perfusion parameter is calculated based on the perfusion parameters of one or more region units which are selected from the first set of region units and located in that segment.

In some other embodiments, a cluster analysis is performed for each segment of the plurality of segments of the imaging region to get a first set of region units corresponding to normal tissue in that segment. Then, for each segment, one or more region units are selected from the first of the region units for that segment, and the corresponding reference perfusion parameter is calculated based on the selected one or more region units.

The technique processes described herein may be implemented by various means. For example, these techniques may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. In the case of a software implementation, use can be made of modules (e.g., procedures, functions, and so on) that perform the functions described herein. The software codes may be stored in a memory unit and executed by the processors.

Moreover, aspects of the claimed subject matter may be implemented as a method, apparatus, system, or article of manufacture using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope of what is described herein.

As used in this application, the terms "calculator", "selector" and "encoder" such as "time-intensity curve calculator", "perfusion parameter calculator", "reference perfusion parameter calculator", "ratio calculator" and "imaging encoder" are intended to refer to a processor or a computer-related entity, either hardware, a combination of hardware and software, software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. An ultrasound imaging system, comprising:
   an ultrasound probe configured to acquire a sequence of ultrasound data of an imaging region of a subject when a contrast agent is perfused in the imaging region;
   a time-intensity curve calculator configured to calculate a time-intensity curve of the contrast agent for each region unit of a plurality of region units of the imaging region, based on the acquired sequence of ultrasound data, each region unit comprising one or more points of the imaging region;
   a reference selector configured to select, among the plurality of region units, a first, second and third set of region units respectively corresponding to normal tissue, vessel and background noise, based on the time-intensity curves, and wherein the reference selector is further configured to divide the imaging region into a plurality of segments, each segment being located at a different depth level and to select the one or more region units from the first set of region units, the one or more region units being located in the segment where the region of interest is located;
   a perfusion parameter calculator configured to calculate a perfusion parameter for each of one or more region units of the first set of region units and a perfusion parameter for a region of interest in the imaging region, based on the calculated time-intensity curves;
   a reference perfusion parameter calculator configured to calculate a reference perfusion parameter, based on the perfusion parameters of the one or more region units located in the segment where the region of interest is located; and
   a ratio calculator configured to calculate a ratio value for the region of interest as a ratio of the perfusion parameter of the region of interest and the reference perfusion parameter.

2. The ultrasound imaging system of claim 1, wherein the reference selector is configured to select the first, second and third sets of region units based on dynamic behavior of the calculated time-intensity curves.

3. The ultrasound imaging system of claim 2, wherein the reference selector is configured to select the first, second and third sets of region units based on at least one feature indicating the dynamic behavior of the time-intensity curves.

4. The ultrasound imaging system of claim 2, wherein the reference selector is configured to select the first, second and third sets of region units by inputting the time-intensity curves of the plurality of region units into a clustering analyzer.

5. The ultrasound imaging system of claim 2, wherein the reference selector is configured to select the first, second and third sets of region units based on predetermined initial first, second and third sets of region units.

6. The ultrasound imaging system of claim 5, wherein the reference selector is configured to determine the predetermined initial first, second and third sets of region units based on one or more statistics about a feature of the time-intensity curve for the plurality of region units.

7. The ultrasound imaging system of claim 6, wherein the feature of the time-intensity curve is one of: area under curve, peak intensity value and mean intensity value, and the one or more statistics comprise mean and standard deviation.

8. The ultrasound imaging system of claim 1, wherein
   the perfusion parameter calculator is further configured to calculate a perfusion parameter for each region unit of the plurality of region units; and
   the ratio calculator is further configured to calculate, for each region unit, a ratio value as a ratio of the perfusion parameter of the region unit and the reference perfusion parameter.

9. The ultrasound imaging system of claim 1, further comprising:
   an image encoder configured to produce corresponding display values for the ratio values; and
   a display configured to display the display values.

10. The ultrasound imaging system of claim 9, wherein the image encoder is further configured to encode ratio values with distinctive coloring or shading.

11. An ultrasound imaging method, comprising:
    acquiring a sequence of ultrasound data of an imaging region of a subject when a contrast agent is perfused in the imaging region;
    calculating a time-intensity curve of the contrast agent for each region unit of a plurality of region units of the imaging region, based on the acquired sequence of ultrasound data, each region unit comprising one or more points of the imaging region, wherein the plurality of region units are located at a plurality of depths of the imaging region;
    selecting, among the plurality of region units, a first, second and third set of region units respectively corresponding to normal tissue, vessels and background noise, based on the time-intensity curves;
    calculating a perfusion parameter for each of one or more region units of the first set of region units and a perfusion parameter for a region of interest in the imaging region, based on the calculated time-intensity curves;
    calculating a reference perfusion parameter, based on the perfusion parameters of the one or more region units located at a depth of the plurality of depths where the region of interest is located; and calculating a ratio value for the region of interest as a ratio of the perfusion parameter of the region of interest and the reference perfusion parameter.

12. An apparatus for calculating a perfusion parameter ratio for a region of interest in an imaging region, comprising:

a receiver configured to receive a time-intensity curve of the contrast agent for each region unit of a plurality of region units of the imaging region, each region unit comprising one or more points of the imaging region;

a reference selector configured to select, among the plurality of region units, a first, second and third set of region units respectively corresponding to normal tissue, vessel and background noise, based on the time-intensity curves, wherein the reference selector is further configured to divide the imaging region into a plurality of segments, each segment being located at a different depth level and to select the one or more region units from the first set of region units, the one or more region units being located in the segment where a region of interest is located;

a perfusion parameter calculator configured to calculate a perfusion parameter for each of one or more region units of the first set of region units and a perfusion parameter for the region of interest, based on the calculated time-intensity curves;

a reference perfusion parameter calculator configured to calculate a reference perfusion parameter, based on the perfusion parameters of the one or more region units located in the segment where the region of interest is located; and a ratio calculator configured to calculate a ratio value for the region of interest as a ratio of the perfusion parameter of the region of interest and the reference perfusion parameter.

13. A method of calculating a perfusion parameter ratio for a region of interest in an imaging region, comprising:

receiving a time-intensity curve of a contrast agent for each region unit of a plurality of region units of an imaging region of a subject, each region unit comprising one or more points of the imaging region, wherein the plurality of region units are located at a plurality of depths of the imaging region;

selecting, among the plurality of region units, a first, second and third set of region units respectively corresponding to normal tissue, vessel and background noise, based on the time-intensity curves;

calculating a perfusion parameter for each of one or more region units of the first set of region units and a perfusion parameter for a region of interest, based on the calculated time-intensity curves;

calculating a reference perfusion parameter based on the perfusion parameters of the one or more region units located at a depth of the plurality of depths where the region of interest is located; and calculating a ratio value for the region of interest as a ratio of the perfusion parameter of the region of interest and the reference perfusion parameter.

14. A computer product, comprising computer program instructions, which, when being executed, performs the method of claim 13.

* * * * *